(12) United States Patent
Malek

(10) Patent No.: US 8,119,111 B2
(45) Date of Patent: *Feb. 21, 2012

(54) TOPICAL ADMINISTRATION CARRIER COMPOSITION AND THERAPEUTIC FORMULATIONS COMPRISING SAME

(75) Inventor: Shane Malek, Las Vegas, NV (US)

(73) Assignee: Celmatrix Corporation, Las Vegas, NV (US)

( * ) Notice: Subject to any disclaimer, the term of this patent is extended or adjusted under 35 U.S.C. 154(b) by 19 days.

This patent is subject to a terminal disclaimer.

(21) Appl. No.: 12/831,241

(22) Filed: Jul. 6, 2010

(65) Prior Publication Data

US 2010/0298365 A1   Nov. 25, 2010

Related U.S. Application Data

(63) Continuation of application No. 11/610,322, filed on Dec. 13, 2006, now Pat. No. 7,749,489, which is a continuation-in-part of application No. 11/305,647, filed on Dec. 16, 2005.

(51) Int. Cl.
*A61K 31/132* (2006.01)
*A61K 8/00* (2006.01)

(52) U.S. Cl. ............ 424/70.31; 424/401; 514/644

(58) Field of Classification Search .................. None
See application file for complete search history.

(56) References Cited

U.S. PATENT DOCUMENTS

| | | |
|---|---|---|
| 3,215,602 A | 11/1965 | Diamond et al. |
| 3,306,824 A | 2/1967 | Laasko et al. |
| 3,317,380 A | 5/1967 | Veldkamp et al. |
| 3,427,382 A | 2/1969 | Haefele |
| 3,729,568 A | 4/1973 | Kligman |
| 4,021,574 A | 5/1977 | Bollag et al. |
| 4,034,114 A | 7/1977 | Yu et al. |
| 4,139,619 A | 2/1979 | Chidsey, III |
| 4,170,229 A | 10/1979 | Olson |
| 4,185,099 A | 1/1980 | Sorbini |
| 4,201,235 A | 5/1980 | Ciavatta |
| 4,405,525 A | 9/1983 | Knight et al. |

(Continued)

FOREIGN PATENT DOCUMENTS

WO        9702041 A1      1/1997

(Continued)

OTHER PUBLICATIONS

Dethlefs, J., et al, "Zur wirking einer vitamin-aminosaure-kombination auf das haarwachstum", "Z. Allgemeinmedzin (German)", 1977, pp. 684-688, vol. 12.

(Continued)

*Primary Examiner* — Frederick Krass
*Assistant Examiner* — Brian Gulledge
(74) *Attorney, Agent, or Firm* — Hultquist, PLLC; Steven J. Hultquist; Kelly K. Reynolds

(57) ABSTRACT

A topical administration carrier composition including water, glycerin and polysorbate, suitable for use in formulations with active ingredient compositions containing active ingredients such as minoxidil that are susceptible to systemic penetration, and solvents that are susceptible to evaporative loss, when the active ingredient composition is topically applied to the body. The carrier formulation retards the evaporative losses of the solvent component(s) and systemic migration losses of the active ingredient composition, to provide sustained topical action, in relation to formulations lacking the carrier composition of the invention.

10 Claims, 1 Drawing Sheet

U.S. PATENT DOCUMENTS

| | | | |
|---|---|---|---|
| 4,820,512 A * | 4/1989 | Grollier | 514/256 |
| 4,855,294 A | 8/1989 | Patel et al. | |
| 5,030,442 A | 7/1991 | Uster et al. | |
| 5,183,817 A | 2/1993 | Bazzano | |
| 5,270,035 A | 12/1993 | Chimento | |
| 5,514,672 A | 5/1996 | Bazzano | |
| 5,733,572 A | 3/1998 | Unger et al. | |
| 5,750,108 A | 5/1998 | Edwards | |
| 5,800,807 A | 9/1998 | Hu et al. | |
| 5,824,295 A | 10/1998 | Syed et al. | |
| 5,843,415 A | 12/1998 | Klar | |
| 5,853,706 A | 12/1998 | Klar | |
| 5,917,021 A | 6/1999 | Lee | |
| 5,951,991 A | 9/1999 | Wagner et al. | |
| 5,972,345 A | 10/1999 | Chizick et al. | |
| 6,156,295 A | 12/2000 | Shah | |
| 6,255,313 B1 | 7/2001 | Suzuki et al. | |
| 6,284,234 B1 | 9/2001 | Niemiec et al. | |
| 6,379,688 B2 | 4/2002 | Yamaguchi et al. | |
| 6,589,514 B2 | 7/2003 | Jensen et al. | |
| 6,596,266 B2 | 7/2003 | Catalfo et al. | |
| 6,723,309 B1 | 4/2004 | Deane | |
| 6,946,120 B2 | 9/2005 | So et al. | |
| 7,749,489 B2 * | 7/2010 | Malek | 424/70.31 |
| 2001/0031286 A1 | 10/2001 | Porras et al. | |
| 2002/0009423 A1 | 1/2002 | Murad | |
| 2002/0048558 A1 | 4/2002 | Niemiec et al. | |
| 2002/0053537 A1 | 5/2002 | Lucido et al. | |
| 2003/0007941 A1 | 1/2003 | Cornelius et al. | |
| 2003/0053971 A1 | 3/2003 | Carson et al. | |
| 2003/0077297 A1 | 4/2003 | Chen et al. | |
| 2003/0092754 A1 | 5/2003 | Nishimuta et al. | |
| 2003/0199644 A1 | 10/2003 | Kim et al. | |
| 2004/0141935 A1 | 7/2004 | Styczynski et al. | |
| 2004/0157766 A1 | 8/2004 | Embil et al. | |
| 2004/0204433 A1 | 10/2004 | Imamura et al. | |
| 2004/0254252 A1 | 12/2004 | Engles et al. | |
| 2005/0049232 A1 | 3/2005 | Lindau | |
| 2005/0079139 A1 | 4/2005 | Jacques et al. | |
| 2005/0163811 A1 | 7/2005 | Lee et al. | |
| 2005/0186164 A1 | 8/2005 | Akyuz | |
| 2005/0238675 A1 | 10/2005 | Li et al. | |
| 2007/0141004 A1 | 6/2007 | Malek | |

FOREIGN PATENT DOCUMENTS

| | | |
|---|---|---|
| WO | 02011698 A1 | 2/2002 |

OTHER PUBLICATIONS

Dethlefs, J., et al., "Effect of a combination of vitamin and amino acid on the hair growth", "Z. Allgemeinmedzin (German)", 1977, pp. 684-688, vol. 1 (English Translation of Abstract Only).

Much, T., "Treatment of alopecia areata with vitamin A acid", "Z. Hautkr. (German)", Dec. 1, 1976, pp. 993-998, vol. 51, No. 23.

Much, T., "Treatment of alopecia areata with vitamin A acid", "Z. Hautkr. (German)", Dec. 1, 1976, pp. 993-998, vol. 51, No. 23 (English Translation of Abstract Only).

Olsen, E. et al., "A rendomized clinical trial of 5% topical minoxidil versus 2% topical minoxidil and placebo in the treatment of androgen", "Journal of Am. Academy of Dermatology", Sep. 2002, pp. 377-385, vol. 47, No. 3, Aug. 23, 2011.

Rook, Arthur, "Some chemical influences on hair growth and pigmentation", "Brit. J. Derm.", Mar. 1965, pp. 115-129, vol. 77, No. 3.

Sawaya, Marty E., "Novel agents for the treatment of alopecia ", "Seminars in Cutaneous Medicine and Surgery", Dec. 1998, pp. 276-283, vol. 17, No. 4.

Fisher, A., "Use of Glycerin in Topical Minoxidil Solutions for Patients Allergic to Propylene Glycol", "Cutis", Feb. 1990, pp. 81-82, vol. 45, No. 2.

* cited by examiner

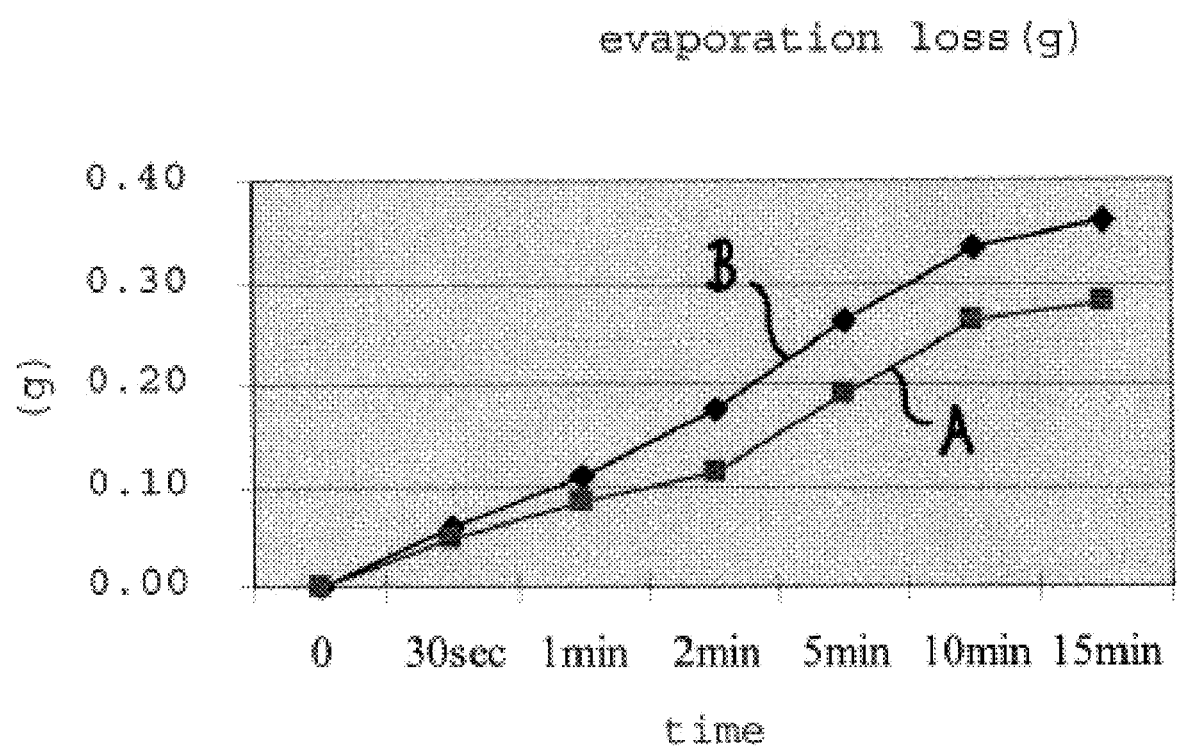

TOPICAL ADMINISTRATION CARRIER COMPOSITION AND THERAPEUTIC FORMULATIONS COMPRISING SAME

CROSS-REFERENCE TO RELATED APPLICATION

This is a continuation of U.S. patent application Ser. No. 11/610,322 filed Dec. 13, 2006 in the name of Shane Malek for "TOPICAL ADMINISTRATION CARRIER COMPOSITION AND THERAPEUTIC FORMULATIONS COMPRISING SAME, issued Jul. 6, 2010 as U.S. Pat. No. 7,749, 489, which in turn is a continuation-in-part of U.S. patent application Ser. No. 11/305,647 filed Dec. 16, 2005 in the name of Shane Malek for "TOPICAL ADMINISTRATION CARRIER COMPOSITION AND THERAPEUTIC FORMULATIONS COMPRISING SAME." Priority of U.S. patent application Ser. No. 11/305,647 and U.S. patent application Ser. No. 11/305,647 is claimed under the provisions of 35 USC 120. The disclosures of U.S. patent application Ser. No. 11/305,647 and U.S. patent application Ser. No. 11/305, 647 are hereby incorporated by reference herein, for all purposes.

FIELD OF THE INVENTION

The present invention relates to topical administration carrier compositions for use in preparing formulations including therapeutic agents and other active ingredients, for administration to scalp, skin and other topical areas of the body, as well as to formulations including such carrier compositions.

BACKGROUND OF THE INVENTION

In the formulation of carriers for topical administration of therapeutic agents and other active ingredients, a wide variety of formulation components are employed, which are in many cases specifically adapted to the particular active ingredient to be applied.

A significant problem in the topical administration of many active ingredient compositions is that they are highly volatile in character. In consequence, evaporative losses of solvents from the active ingredient compositions are significant, and result in diminution of the treatment efficacy of such ingredient compositions. Evaporative loss of solvents from the active ingredient compositions therefore may severely diminish the therapeutic effect and/or duration of benefit of the active ingredient on the areas of the body to which the formulation has been topically applied.

As a result, increased amounts of the topical composition may need to be applied, to ensure the beneficial effect. This may in turn lead to gross overuse of the composition, in an effort to provide surplus material to compensate for evaporative losses from the active ingredient composition.

Another problem that frequently occurs in use of topical compositions, e.g., skin treatments, hair treatments, hair growth compositions, cuticle treatments, and the like, is that the active ingredient may be highly susceptible to systemic migration. By systemic migration is meant that the active topical agent penetrates through the skin, hair, nails, etc. into the system of the user, with consequent loss of surface activity of the active ingredient(s). As in the case of evaporative loss, systemic migration diminishes the beneficial effect of the active ingredient, with the same consequences as those discussed above in respect of evaporative loss of solvents.

Additionally, such systemic migration may result in systemic toxicity effects deriving from the active ingredient(s) intended to remain on the surface of the skin, scalp, hair, etc., which nonetheless pass into the body through the skin, hair follicles, and/or other systemic portals, to internal locales in the user's body where the active ingredient is not desired and where it may in fact contribute to adverse physiological side-effects. For example, a substantial proportion of daily users of commercially available 5% minoxidil formulations report incidences of heart palpitations 10-30 minutes after use and scalp irritation 1-2 hours after use.

There is therefore a continuing effort in the field of topical compositions containing active ingredients susceptible to such deficiencies, to develop improved compositions that retard evaporative loss of solvents from the formulation and that minimize systemic penetration of active ingredients.

SUMMARY OF THE INVENTION

The present invention relates to topical administration carrier compositions that are usefully employed in preparing formulations of active ingredients for topical administration to the body, e.g., to the skin, hair, etc.

The present invention relates to a topical administration carrier composition suitable for use with active ingredient compositions that are otherwise susceptible to evaporative loss of solvents and systemic migration of active ingredients when topically applied to the body.

The topical administration carrier composition of the invention contains as ingredients water, glycerin and polysorbate, in relative proportions to one another that reduce the evaporative loss of solvent and systemic migration of active ingredient that would otherwise occur in the absence of such carrier. The topical administration carrier composition can alternatively consist, or consist essentially of, such water, glycerin and polysorbate components, in various embodiments.

The invention relates in one aspect to a carrier composition containing water, glycerin and polysorbate-80, in relative proportions to one another so that the carrier composition retards (i) volatilization of solvent(s) and (ii) system migration of topically active agent(s), in formulations containing active ingredient(s) otherwise susceptible to systemic migration and solvent(s) otherwise susceptible to evaporative loss.

In another aspect, the invention relates to a carrier composition, comprising:
 40-70 weight percent water;
 20-40 weight percent glycerin; and
 5-15 weight percent polysorbate-80
wherein the weight percents of such ingredients are based on the total weight of the water, glycerin and polysorbate-80 in the carrier composition.

In a further embodiment, the invention relates to a carrier composition, comprising:
 from 55 to 60 weight percent water;
 from 30 to 35 weight percent glycerin; and
 from 8 to 12 weight percent polysorbate-80.
wherein the weight percents of such ingredients are based on the total weight of the water, glycerin and polysorbate-80 in the carrier composition.

Another aspect of the invention relates to a carrier composition containing the following ingredients: water, glycerin, polysorbate 80, retinol, serenoa serrulata fruit extract, beta-sitosterol, panthenol, cystine, biotin, polysorbate-20, DMDM hydantoin, methylparaben.

A further aspect of the invention relates to a method of formulating a topical composition containing at least one active ingredient that is susceptible to undesired systemic penetration from a topical locus and solvent that is susceptible to evaporative loss from such topical locus, wherein the method comprises incorporating the active ingredient(s) in a formulation including the carrier composition of the invention.

Another aspect of the invention relates to a minoxidil formulation having the following composition by weight, based on total weight of the formulation:

| | |
|---|---|
| Minoxidil | 1-10% |
| Glycerin | 18-30% |
| Polysorbate 80 | 4-16% |
| Retinol Palmetate | 0.01-0.1% |
| Beta-sitosterol | 0.0001-0.001% |
| Panthenol | 0.001-0.01% |
| DMDM-Hydantoin | 0.02-0.2% |
| Methylparaben | 0.01-0.2% |
| Ethanol | 30-50% |
| Water | 10-25% | wherein the percentage weights of all ingredients totals to 100 weight percent.

A specific aspect of the invention relates to a minoxidil formulation having the following composition by weight, based on total weight of the formulation:

| | |
|---|---|
| Minoxidil | 5% |
| Glycerin | 24.5% |
| Polysorbate 80 | 7.6% |
| Retinol Palmetate | 0.05% |
| Beta-sitosterol | 0.0004% |
| Panthenol | 0.004% |
| DMDM-Hydantoin | 0.073% |
| Methylparaben | 0.09% |
| Ethanol | 44.2% |
| Water | 17% |

Another specific aspect of the invention relates to a minoxidil formulation having the following composition by weight, based on total weight of the formulation:

| | |
|---|---|
| Minoxidil | 2% |
| Glycerin | 24.5% |
| Polysorbate 80 | 7.6% |
| Retinol Palmetate | 0.05% |
| Beta-sitosterol | 0.0004% |
| Panthenol | 0.004% |
| DMDM-Hydantoin | 0.073% |
| Methylparaben | 0.09% |
| Ethanol | 44.2% |
| Water | 20% |

Another aspect of the invention relates to a minoxidil formulation having the following composition by weight, based on total weight of the formulation:

| | |
|---|---|
| Minoxidil | 1-10% |
| Glycerin | 15-35% |
| Polysorbate 80 | 2-20% |
| Propylene glycol | 0-40% |
| Ethanol or other alcohol | 10-50% |
| Water | 5-35% |
| Optional Additional Ingredients | 0-3% |
| (optional ingredients including, for example, retinol and/or other retinoid compound(s), betasitosterol, panthenol, DMDM-hydantoin, biotin, cystine, sabal seralata fruit extract or other saw palmetto compounds, methyl paraben or other preservative(s)) | | wherein the total weight percents of all ingredients in the formulation total to 100 weight percent.

A further aspect of the invention relates to a two-package hair growth formulation, including an active ingredient composition, Composition A, and a carrier composition, Composition B, in which Composition A has the following composition by weight:

| Composition A | |
|---|---|
| Water | 10-22% wt. |
| Propylene glycol or other glycol | 40-60% wt. |
| Ethanol or other alcohol | 20-30% wt. |
| Minoxidil | 1-10% wt. |
| TOTAL | 100.00% wt. | and Composition B has the following composition by weight:

| Composition B | |
|---|---|
| Water | 40-60% wt |
| Glycerin | 20-40% wt. |
| Polysorbate 80 | 5-15% wt. |
| Optional Additional Ingredients | 0-3% |
| (optional ingredients including, for example, retinol and/or other retinoid compound(s), betasitosterol, panthenol, DMDM-hydantoin, biotin, cystine, sabal seralata fruit extract or other saw palmetto compounds, methyl paraben or other preservative(s)) | |
| TOTAL | 100.00% wt. |

A still further aspect of the invention relates to a two-package hair growth formulation, including an active ingredient composition, Composition A, and a carrier composition, Composition B, in which Composition A has the following constitution:

| Composition A | |
|---|---|
| Water | 15.959% wt. |
| Propylene glycol | 52.803% wt. |
| Ethanol | 26.141% wt. |
| Minoxidil | 5.097% wt. |
| TOTAL | 100.00% wt. | and Composition B has the following constitution:

| Composition B | |
|---|---|
| Water | 56.227% wt |
| Glycerin | 32.740% wt. |
| Methylparaben | 0.250% wt. |
| Panthenol | 0.010% wt. |
| DMDM hydantoin | 0.200% wt. |
| sabal seralata fruit extract | 0.010% wt. |
| polysorbate 80 | 10.260% wt. |
| beta sitosterol | 0.001% wt. |

-continued

| Composition B | |
|---|---|
| biotin | 0.001% wt. |
| cystine | 0.001% wt. |
| retinol | 0.300% wt. |
| TOTAL | 100.00% wt. |

Another aspect of the invention relates to a method of increasing efficacy of an alcoholic minoxidil composition in topical application to the scalp, comprising formulating said alcoholic minoxidil composition with an aqueous carrier composition containing glycerin and polysorbate-80.

Additional objects, features and advantages of the invention will be readily apparent from the description that follows, and readily derivable by empirical determination without undue effort, based on the description herein.

DETAILED DESCRIPTION OF THE INVENTION, AND PREFERRED EMBODIMENTS THEREOF

The present invention relates to topical administration carrier compositions suitable for use with active ingredient compositions that are susceptible to evaporative loss of solvent(s) and systemic migration of active ingredient(s), when topically applied to the body.

The carrier compositions of the invention are formulated with such active ingredient compositions to achieve reduced evaporative loss of solvent(s), and reduced systemic migration of active ingredient(s), in relation to evaporative and systemic migration losses that would otherwise occur in the absence of such carrier composition.

The topical administration carrier composition of the invention contains as components water, glycerin and polysorbate, in relative proportions to one another that reduce the evaporative loss of solvent and systemic migration of active ingredient that would otherwise occur in the absence of such carrier.

The topical administration carrier composition can alternatively comprise, consist, or consist essentially of, such water, glycerin and polysorbate components.

The invention provides a simple and effective carrier composition that has been found to be highly effective in application to active ingredients such as hair growth promoters.

Such carrier composition has particular applicability for active ingredients such as minoxidil, to reduce evaporative solvent loss from the formulation and systemic migration of the active ingredient from the scalp areas to which the formulation is applied, in relation to prior art minoxidil formulations that are susceptible to such solvent loss and systemic migration.

In one embodiment, the carrier composition of the invention contains water, glycerin and polysorbate-80, e.g., in amounts of:
40-70 weight percent water;
20-40 weight percent glycerin; and
5-15 weight percent polysorbate-80
wherein the weight percents of such ingredients are based on the total weight of the water, glycerin and polysorbate-80 in the carrier composition and the weight percentages of all components total to 100 weight percent.

In a specific embodiment of such carrier composition, the composition may be formulated with additional optional ingredients, including, for example, panthenol, cysteine, 3-betasitosterol, 4-retinol, biotin, fruit extracts, syrups, and the like, preservatives (e.g., methylparabin), DMDM hydantoin, polysorbate-20 (as an adjuvant stabilizer for retinol, when retinol is present in the composition), and the like.

In a specific embodiment, the topical carrier composition includes the following ingredients:
50-60 weight percent water;
28-35 weight percent glycerin; and
7-15 weight percent polysorbate-80
wherein the weight percents of such ingredients are based on the total weight of the water, glycerin and polysorbate-80 in the carrier composition and the weight percentages of all components total to 100 weight percent.

In another carrier composition embodiment of the invention, water is present in an amount of 55-60 weight percent, glycerin is present in an amount of from 30-35 weight percent, and polysorbate-80 is present is an amount of from 8-12 weight percent wherein the weight percents of such ingredients are based on the total weight of the water, glycerin and polysorbate-80 in the carrier composition and the weight percentages of all components total to 100 weight percent.

It will be recognized that essential ingredients of the compositions of the invention can be varied in relative proportions to one another, and that various formulations can be made up, as appropriate to specific active ingredient(s) to be utilized with the carrier for topical use.

As mentioned, the carrier of the present invention can comprise, consist, or consist essentially of, the water, glycerin and polysorbate components described hereinabove as essential components of such carrier composition.

In further specific embodiments of the invention, the essential ingredients of water, glycerin and polysorbate can be variously supplemented with further additives, including those illustratively mentioned hereinabove. In one embodiment, such additives include one or more of pathenol, cysteine, betasitosterol and retinol. In a further embodiment, two or more of such additives are incorporated in the carrier composition, and in other embodiments at least three of such components are present, with still other compositions including all four of such additives.

The carrier formulations of the invention may be constituted in a wide variety of forms, depending on the extent of evaporative loss of solvent(s) and systemic migration of active ingredient(s) that would otherwise occur if the active ingredient composition were not formulated with a carrier composition of the present invention.

Accordingly, the formulation of the invention may be readily empirically established for a particular active ingredient composition susceptible to such evaporative and systemic modes of loss, without undue experimentation, based on the disclosure herein, by simple empirical procedures to assess such evaporative and systemic migration losses, in the active ingredient composition per se, as well as when the active ingredient composition is mixed with the carrier composition of the invention. Suitable empirical procedures include those illustratively set forth hereinafter, in the examples hereof.

In one illustrative embodiment of the invention, the carrier composition includes the following ingredients:
Water
Glycerin
Polysorbate 80
Retinol
Serenoa Serrulata Fruit Extract
Betasitosterol
Panthenol
Cystine
Biotin
Polysorbate 20

DMDM Hydantoin
Methylparaben

The active ingredient(s) with which the carrier is useful include a wide variety of topical agents. One preferred class of active ingredients comprises hair care and head care products, including hair growth promoters, hair damage rejuvenating agents, hair care cosmetic agents, scalp treatment products, shampoos, sunscreens and sun blocks, etc. One preferred application for the carrier compositions of the present invention is as a vehicle for formulation of minoxidil, and application of the resulting minoxidil formulation to the scalp, as a hair growth promoter.

In such preferred application for use of minoxidil as a hair growth promoter, the carrier composition of the present invention serves to neutralize the alcoholic properties of the minoxidil solution, so that the overall formulation remains in liquid form for a longer period of time and does not sustain rapid loss of alcohol or other volatile components, and so that the active ingredient minoxidil does not undergo excessive systemic migration into the user's body, e.g., into the bloodstream, but rather remains at the scalp to act at the follicle.

In the same way, the carrier composition of the present invention can be used with other active ingredient compositions containing alcoholic or other volatile components, in order to reduce evaporative loss of the volatile components from the active ingredient composition, and to reduce systemic migration of the active ingredient and/or other components of the active ingredient composition, in order to achieve sustained presence/persistence of the active ingredient composition on the body for purposes of therapeutic intervention, cosmetic enhancement, etc.

In general, minoxidil-containing formulations of the invention can incorporate the carrier composition at any suitable ratio of the carrier composition to the active ingredient composition to yield a desired concentration of minoxidil. Typically, concentrations of minoxidil in the range of from about 0.1 weight percent to about 15 weight percent or more are generally useful, and with preferred concentrations of minoxidil in the formulation can for example be on the order of from about 0.5 weight percent to 10 weight percent, based on the weight of the formulation. Other embodiments within the general scope of the invention utilize minoxidil in varying ranges, such as in a range of 1-7 wt %, 2-6 wt %, 3-6 wt %, and 4-6 wt %, based on the total weight of the formulation.

The minoxidil-containing formulations of the invention may be employed as part of a continuing program of use of minoxidil, in which such formulations are applied to the scalp at regular intervals, as for example twice daily each day, in an amount of 0.5-2 mL of the formulation in each administration.

By way of example, the minoxidil formulation may have the following composition by weight, based on total weight of the formulation:

| | |
|---|---|
| Minoxidil | 1-10% |
| Glycerin | 15-35% |
| Polysorbate 80 | 2-20% |
| Propylene glycol | 0-40% |
| Ethanol or other alcohol | 10-50% |
| Water | 5-35% |
| Optional Additional Ingredients (optional ingredients including, for example, retinol and/or other retinoid compound(s), betasitosterol, panthenol, DMDM-hydantoin, biotin, cystine, sabal seralata fruit extract or other saw palmetto compounds, methyl paraben or other preservative(s)) | 0-3% | wherein the total weight percents of all ingredients in the formulation total to 100 weight percent.

Minoxidil formulations of the invention may be provided as a two-package hair growth formulation, including an active ingredient composition, Composition A, and a carrier composition, Composition B, in which Composition A has the following composition by weight:

| Composition A | |
|---|---|
| Water | 10-22% wt. |
| Propylene glycol or other glycol | 40-60% wt. |
| Ethanol or other alcohol | 20-30% wt. |
| Minoxidil | 1-10% wt. |
| TOTAL | 100.00% wt. | and Composition B has the following composition by weight:

| Composition B | |
|---|---|
| Water | 40-60% wt |
| Glycerin | 20-40% wt. |
| Polysorbate 80 | 5-15% wt. |
| Optional Additional Ingredients (optional ingredients including, for example, retinol and/or other retinoid compound(s), betasitosterol, panthenol, DMDM-hydantoin, biotin, cystine, sabal seralata fruit extract or other saw palmetto compounds, methyl paraben or other preservative(s)) | 0-3% |
| TOTAL | 100.00% wt. |

One illustrative minoxidil-containing hair growth composition of the invention is provided as a two-part package formulation, including an active ingredient composition, Composition A, and a carrier composition, Composition B, in which Composition A has the following makeup:

| Composition A | |
|---|---|
| Water | 15.959% wt. |
| Propylene glycol | 52.803% wt. |
| Ethanol | 26.141% wt. |
| Minoxidil | 5.097% wt. |
| TOTAL | 100.00% wt. | and Composition B has the following makeup:

| Composition B | |
|---|---|
| Water | 56.227% wt |
| Glycerin | 32.740% wt. |
| Methylparaben | 0.250% wt. |
| Panthenol | 0.010% wt. |
| DMDM hydantoin | 0.200% wt. |
| sabal seralata fruit extract | 0.010% wt. |
| polysorbate 80 | 10.260% wt. |
| beta sitosterol | 0.001% wt. |
| biotin | 0.001% wt. |
| cystine | 0.001% wt. |
| retinol | 0.300% wt. |
| TOTAL | 100.00% wt. |

In use, Composition A and Composition B are mixed together, in a mixing ratio of two parts by volume of Composition A (active ingredient composition) to one part by volume of Composition B (carrier composition).

This (2 parts by volume Composition A: 1 part by volume Composition B) formulation is referred to hereinafter as the Vitadil/Nutrisol Formulation.

Set out below is a tabulation of the Composition B ingredients and corresponding trade names, for a preferred embodiment of the invention.

| Composition B | | |
|---|---|---|
| Name | Trade Name | Wt. % |
| Water | Purified Water | 56.227 |
| Glycerin | Glycerin 99.7% | 32.740 |
| Methylparaben, NF | Methylparaben, NF | 0.250 |
| Panthenol | Ritapan DL | 0.010 |
| DMDM Hydantoin | Mackstat DM | 0.200 |
| Glycerin and Sabal Seralata Fruit Extract | Actiphyte of Saw Palmetto | 0.010 |
| Polysorbate 80 | Tween 80 | 10.260 |
| Beta-Sitosterol | Beta-Sitosterol | 0.001 |
| Biotin, USP | Biotin, USP | 0.001 |
| Cystine, FCC | Cystine, FCC | 0.001 |
| Retinol and Polysorbate 20 | Retinol 50C | 0.300 |

In another aspect, the invention contemplates minoxidil formulations having the following range of ingredient concentrations:

| Minoxidil formulation (w/w) | |
|---|---|
| Minoxidil | 1-10% |
| Glycerin | 18-30% |
| Retinol Palmetate | 0.01-0.1% |
| Polysorbate 80 | 4-16% |
| Beta-sitosterol | 0.0001-0.001% |
| Panthenol | 0.001-0.01% |
| DMDM-Hydantoin | 0.02-0.2% |
| Methylparaben | 0.01-0.2% |
| Ethanol | 30-50% |
| Water | 10-25% | wherein the weight percentages of all ingredients totals to 100 weight percent.

In a specific embodiment, a minoxidil formulation in accordance with the invention may have the following composition:

| Minoxidil 5% solution (w/w) | |
|---|---|
| Minoxidil | 5% |
| Glycerin | 24.5% |
| Polysorbate 80 | 7.6% |
| Retinol Palmetate | 0.05% |
| Beta-sitosterol | 0.0004% |
| Panthenol | 0.004% |
| DMDM-Hydantoin | 0.073% |
| Methylparaben | 0.09% |
| Ethanol | 44.2% |
| Water | 17% |

Such formulation may for example be particularly suited for male subjects seeking hair growth such as in the treatment of male pattern baldness.

In another embodiment, a minoxidil formulation in accordance with the invention has a same composition as above, except containing 2% minoxidil and 20% water, instead of 5% minoxidil and 17% water. This formulation is identified below as to its ingredients.

| Minoxidil 2% solution (w/w) | |
|---|---|
| Minoxidil | 2% |
| Glycerin | 24.5% |
| Polysorbate 80 | 7.6% |
| Retinol Palmetate | 0.05% |
| Beta-sitosterol | 0.0004% |
| Panthenol | 0.004% |
| DMDM-Hydantoin | 0.073% |
| Methylparaben | 0.09% |
| Ethanol | 44.2% |
| Water | 20% |

Such formulation may for example be used in the treatment of female baldness.

In general, the compositions of the invention may be really formed by simple mixture of ingredients under gentle agitation mixing conditions at ambient temperature, to constitute the carrier composition, such as by use of a paddle mixer in a vat or other container, to produce the carrier composition product.

Formulations of the invention may similarly be constituted by mixing of the carrier composition and the active ingredient composition under gentle agitation mixing conditions at ambient temperature.

The features and advantages of the invention are more fully apparent from the following non-limiting examples, wherein all parts and percentages are by weight, unless otherwise expressly stated.

Example 1

Repeated Insult Patch Test

A study was conducted to determine the dermal irritation and sensitization potential of a minoxidil formulation according to the present invention, based on the fact that commercial compositions of minoxidil are known to cause itching, drying and scaling of the skin for almost all users to some extent.

The above-described Vitadil/Nutrisol Formulation of the invention was administered to the test subjects in a transdermal patch (Occlusive Strip with Flexcon®, TrueMed Technologies, Inc., Burnsville, Minn.) containing such minoxidil formulation.

The test subjects (male and female) were selected based on the following criteria: age between 18 and 70; general good health; having no skin diseases that might be confused with a skin reaction from the test material; in the case of females, test subjects not pregnant or lactating; and then subjects not currently using any systemic or topical corticosteroids, anti-inflammatory drugs or antihistamines.

Prior to the application of the patch to the skin of the test subjects, the test area was wiped with 70% isopropyl alcohol and allowed to dry. The test material that was applied to the upper back of each test subject, between the scapulae, was allowed to remain in direct skin contact for a period of 24 hours.

Patches were applied to the same site of each subject on a Monday, Wednesday and Friday for a total of nine applications during the induction period, with modification of the schedule to allow for missed visits or holidays during the testing. If a test subject was unable to report on an assigned test date, the test material was applied on two consecutive days during the induction phase and/or a make up day was added at the end of the induction phase.

The sites were graded for dermal irritation 24 hours after removal of the patches by the subjects on Tuesday and Thursday and 48 hours after removal of the patches on Saturday, unless the patching schedule was altered as described above.

The sites were graded according to the following scoring system:

| | Normal Scoring Scale |
|---|---|
| 0 | no visible skin reaction |
| ± | barely perceptible erythema (minimal) |
| 1+ | mild erythema (diffuse) |
| 2+ | well-defined erythema |
| 3+ | erythema and edema |
| 4+ | erythema and edema with vesiculation |

If a "2+" reaction or greater occurred, the test material was applied to an adjacent virgin site. If a "2+" reaction or greater occurred on the new site, the subject was not patched again during the induction phase but was challenged on the appropriate day of the study. At the discretion of the study director, patch sites with scores less than "2+" were subject to change to new sites.

Following in approximately a two-week rest period, the challenge patches were applied to previously untreated test sites on the back of each subject. After 24 hours, the patches were removed and the test sites were evaluated for normal reactions. The test sites were re-evaluated at 48 and 72 hours. Subjects exhibiting reactions during the challenge phase of the study may have been asked to return for a 96 hour evaluation.

The study was initiated with 224 subjects. Fourteen subjects discontinued study participation for reasons unrelated to the test material. One subject was discontinued due to a pre-sensitized station to the test material. A total of 209 subjects completed the study.

Based on the test population of 209 subjects, the formulation of the present invention did not demonstrate a clinically significant potential for eliciting a dermal irritation or sensitization.

The test data for the study are set out below.

TABLE 1

Summary of Dermal Scores

| Subject Number | Induction Scores | | | | | | | | | Challenge Scores | | |
|---|---|---|---|---|---|---|---|---|---|---|---|---|
| | 1 | 2 | 3 | 4 | 5 | 6 | 7 | 8 | 9 | 24 Hour | 48 Hour | 72 Hour |
| 1A | 0 | 0 | 0 | 0 | 0 | 0 | ± | ± | ± | 0 | 0 | 0 |
| 2A | 0 | 0 | 0 | 0 | 0 | 0 | 0 | 0 | 0 | 0 | 0 | 0 |
| 3A | 0 | 0 | 0 | 0 | 0 | 0 | 0 | 0 | 0 | 0 | 0 | 0 |
| 4A | 0 | 0 | 0 | 0 | 0 | 0 | 0 | 0 | 0 | 0 | 0 | 0 |
| 5A | 0 | 0 | 0 | 0 | 0 | 0 | 0 | 0 | 0 | 0 | 0 | 0 |
| 6A | 0 | 0 | 0 | 0 | 0 | 0 | 0 | 0 | 0 | 0 | 0 | 0 |
| 7A | 0 | 0 | 0 | 0 | 0 | 0 | 0 | 0 | 0 | 0 | 0 | 0 |
| 8A | 0 | 0 | 0 | 0 | 0 | 0 | 0 | 0 | 0 | 0 | 0 | 0 |
| 9A | 0 | 0 | 0 | 0 | 0 | 0 | 0 | 0 | 0 | 0 | 0 | 0 |
| 10A | 0 | 0 | 0 | 0 | 0 | 0 | 0 | 0 | 0 | 0 | 0 | 0 |
| 11A | 0 | 0 | 0 | 0 | 0 | 0 | 0 | 0 | 0 | 0 | 0 | 0 |
| 12A | 0 | 0 | 0 | 0 | 0 | 0 | 0 | 0 | 0 | 0 | 0 | 0 |
| 13A | 0 | 0 | 0 | 0 | 0 | 0 | 0 | 0 | 0 | 0 | 0 | 0 |
| 14A | 0 | 0 | 0 | 0 | 0 | 0 | 0 | 0 | 0 | 0 | 0 | 0 |
| 15A | 0 | 0 | 0 | 0 | 0 | 0 | 0 | 0 | 0 | 0 | 0 | 0 |
| 16A | 0 | 0 | 0 | 0 | 0 | 0 | 0 | 0 | 0 | 0 | 0 | 0 |
| 17A | 0 | 0 | 0 | 0 | 0 | 0 | 0 | 0 | 0 | 0 | 0 | 0 |
| 18A | 0 | 0 | 0 | 0 | 0 | 0 | 0 | 0 | 0 | 0 | 0 | 0 |
| 19A | 0 | 0 | 0 | 0 | 0 | 0 | 0 | 0 | 0 | 0 | 0 | 0 |
| 20A | 0 | 0 | 0 | 0 | 0 | 0 | 0 | 0 | 0 | 0 | 0 | 0 |
| 21A | 0 | 0 | 0 | 0 | 0 | 0 | 0 | 0 | 0 | 0 | 0 | 0 |
| 22A | 0 | 0 | 0 | 0 | 0 | 0 | 0 | 0 | 0 | 0 | 0 | 0 |
| 23A | 0 | 0 | 0 | 0 | 0 | 0 | 0 | 0 | 0 | 0 | 0 | 0 |
| 24A | 0 | 0 | 0 | 0 | 0 | 0 | 0 | 0 | 0 | 0 | 0 | 0 |
| 25A | 0 | 0 | 0 | 0 | 0 | 0 | 0 | 0 | 0 | 0 | 0 | 0 |
| 26A | 0 | 0 | 0 | 0 | 0 | 0 | 0 | 0 | 0 | 0 | 0 | 0 |
| 27A | 0 | 0 | 0 | 0 | 0 | 0 | 0 | 0 | 0 | 0 | 0 | 0 |
| 28A | 0 | 0 | 0 | 0 | 0 | 0 | 0 | 0 | 0 | 0 | 0 | 0 |
| 29A | 0 | 0 | 0 | 0 | 0 | 0 | 0 | 0 | 0 | 0 | 0 | 0 |
| 30A | 0 | 0 | 0 | 0 | 0 | 0 | 0 | 0 | 0 | 0 | 0 | 0 |
| 31A | 0 | 0 | 0 | 0 | 0 | 0 | 0 | 0 | 0 | 0 | 0 | 0 |
| 32A | 0 | 0 | 0 | 0 | 0 | 0 | 0 | 0 | 0 | 0 | 0 | 0 |
| 33A | 0 | 0 | 0 | 0 | 0 | 0 | 0 | 0 | 0 | 0 | 0 | 0 |
| 34A | 0 | 0 | 0 | 0 | 0 | 0 | 0 | 0 | 0 | 0 | 0 | 0 |
| 35A | 0 | 0 | 0 | 0 | 0 | 0 | 0 | 0 | 0 | 0 | 0 | 0 |
| 36A | 0 | 0 | 0 | 0 | 0 | 0 | 0 | 0 | 0 | 0 | 0 | 0 |
| 37A | 0 | 0 | 0 | 0 | 0 | 0 | 0 | 0 | 0 | 0 | 0 | 0 |
| 38A | 0 | 0 | 0 | 0 | 0 | 0 | 0 | 0 | 0 | 0 | 0 | 0 |
| 39A | 0 | 0 | 0 | 0 | 0 | 0 | 0 | 0 | 0 | 0 | 0 | 0 |
| 40A | 0 | 0 | 0 | 0 | 0 | 0 | 0 | 0 | 0 | 0 | 0 | 0 |
| 41A | 0 | 0 | 0 | 0 | 0 | 0 | 0 | 0 | 0 | 0 | 0 | 0 |
| 42A | 0 | 0 | 0 | 0 | 0 | 0 | 0 | 0 | 0 | 0 | 0 | 0 |

TABLE 1-continued

Summary of Dermal Scores

| Subject Number | Induction Scores ||||||||| Challenge Scores |||
| --- | --- | --- | --- | --- | --- | --- | --- | --- | --- | --- | --- | --- |
| | 1 | 2 | 3 | 4 | 5 | 6 | 7 | 8 | 9 | 24 Hour | 48 Hour | 72 Hour |
| 43A | | | | | | Discontinued | | | | | | |
| 44A | 0 | 0 | 0 | 0 | 0 | 0 | 0 | 0 | 0 | 0 | 0 | 0 |
| 45A | 0 | 0 | 0 | 0 | 0 | 0 | 0 | 0 | 0 | 0 | 0 | 0 |
| 46A | 0 | 0 | 0 | 0 | 0 | 0 | 0 | 0 | 0 | 0 | 0 | 0 |
| 47A | 0 | 0 | 0 | 0 | 0 | 0 | 0 | 0 | 0 | 0 | 0 | 0 |
| 48A | 0 | 0 | 0 | 0 | 0 | 0 | 0 | 0 | 0 | 0 | 0 | 0 |
| 49A | 0 | 0 | 0 | 0 | 0 | 0 | 0 | 0 | 0 | 0 | 0 | 0 |
| 50A | 0 | 0 | 0 | 0 | 0 | 0 | 0 | 0 | 0 | 0 | 0 | 0 |
| 51A | 0 | 0 | 0 | 0 | 0 | 0 | 0 | 0 | 0 | 0 | 0 | 0 |
| 52A | 0 | 0 | 0 | 0 | 0 | 0 | 0 | 0 | 0 | 0 | 0 | 0 |
| 53A | 0 | 0 | 0 | 0 | 0 | 0 | 0 | 0 | 0 | 0 | 0 | 0 |
| 54A | 0 | 0 | 0 | 0 | 0 | 0 | 0 | 0 | 0 | 0 | 0 | 0 |
| 55A | 0 | 0 | 0 | 0 | 0 | 0 | 0 | 0 | 0 | 0 | 0 | 0 |
| 56A | 0 | 0 | 0 | 0 | 0 | 0 | 0 | 0 | 0 | 0 | 0 | 0 |
| 57A | 0 | 0 | 0 | 0 | 0 | 0 | 0 | 0 | 0 | 0 | 0 | 0 |
| 58A | 0 | 0 | 0 | 0 | 0 | 0 | 0 | 0 | 0 | 0 | 0 | 0 |
| 59A | 0 | 0 | 0 | 0 | 0 | 0 | 0 | 0 | 0 | 0 | 0 | 0 |
| 60A | 0 | 0 | 0 | 0 | 0 | 0 | 0 | 0 | 0 | 0 | 0 | 0 |
| 61A | 0 | 0 | 0 | 0 | 0 | 0 | 0 | 0 | 0 | 0 | 0 | 0 |
| 62A | 0 | 0 | 0 | 0 | 0 | 0 | 0 | 0 | 0 | 0 | 0 | 0 |
| 63A | 0 | 0 | 0 | 0 | 0 | 0 | 0 | 0 | 0 | 0 | 0 | 0 |
| 64A | 0 | 0 | 0 | 0 | 0 | 0 | 0 | 0 | 0 | 0 | 0 | 0 |
| 65A | 0 | 0 | 0 | 0 | 0 | 0 | 0 | 0 | 0 | 0 | 0 | 0 |
| 66A | 0 | 0 | 0 | 0 | 0 | 0 | 0 | 0 | 0 | 0 | 0 | 0 |
| 67A | 0 | 0 | 0 | 0 | 0 | 0 | 0 | 0 | 0 | 0 | 0 | 0 |
| 68A | 0 | 0 | 0 | 0 | 0 | 0 | 0 | 0 | 0 | 0 | 0 | 0 |
| 69A | 0 | 0 | 0 | 0 | 0 | 0 | 0 | 0 | 0 | 0 | 0 | 0 |
| 70A | 0 | 0 | | | | | Discontinued | | | | | |
| 71A | 0 | 0 | 0 | 0 | 0 | 0 | 0 | 0 | 0 | 0 | 0 | 0 |
| 72A | 0 | 0 | 0 | 0 | 0 | 0 | 0 | 0 | 0 | 0 | 0 | 0 |
| 73A | 0 | 0 | 0 | 0 | 0 | 0 | 0 | 0 | 0 | 0 | 0 | 0 |
| 74A | 0 | 0 | 0 | 0 | 0 | 0 | 0 | 0 | 0 | 0 | 0 | 0 |
| 75A | 0 | 0 | 0 | 0 | 0 | 0 | 0 | 0 | 0 | 0 | 0 | 0 |
| 76A | | | | | | Discontinued | | | | | | |
| 77A | 0 | 0 | 0 | 0 | 0 | 0 | 0 | 0 | 0 | 0 | 0 | 0 |
| 78A | 0 | 0 | 0 | 0 | 0 | 0 | 0 | 0 | 0 | 0 | 0 | 0 |
| 79A | 0 | 0 | 0 | 0 | 0 | 0 | 0 | 0 | 0 | 0 | 0 | 0 |
| 80A | 0 | 0 | 0 | 0 | 0 | 0 | 0 | 0 | 0 | 0 | 0 | 0 |
| 81A | 0 | 0 | 0 | 0 | 0 | 0 | 0 | 0 | 0 | 0 | 0 | 0 |
| 82A | 0 | 0 | 0 | 0 | 0 | 0 | 0 | 0 | 0 | 0 | 0 | 0 |
| 83A | 0 | 0 | 0 | 0 | 0 | 0 | 0 | 0 | 0 | 0 | 0 | 0 |
| 84A | 0 | 0 | 0 | 0 | 0 | 0 | 0 | 0 | 0 | 0 | 0 | 0 |
| 85A | 0 | 0 | 0 | 0 | 0 | 0 | 0 | 0 | 0 | 0 | 0 | 0 |
| 86A | 0 | 0 | 0 | 0 | 0 | 0 | 0 | 0 | 0 | 0 | 0 | 0 |
| 87A | 0 | 0 | 0 | 0 | 0 | 0 | 0 | 0 | 0 | 0 | 0 | 0 |
| 88A | 0 | 0 | 0 | 0 | 0 | 0 | 0 | | | Discontinued | | |
| 89A | 0 | 0 | 0 | 0 | 0 | 0 | 0 | 0 | 0 | 0 | 0 | 0 |
| 90A | 0 | 0 | 0 | 0 | 0 | 0 | 0 | 0 | 0 | 0 | 0 | 0 |
| 91A | 0 | 0 | 0 | 0 | 0 | 0 | 0 | 0 | 0 | 0 | 0 | 0 |
| 92A | 0 | 0 | 0 | 0 | 0 | 0 | 0 | 0 | 0 | 0 | 0 | 0 |
| 93A | 0 | 0 | 1+ | ± | ± | ± | 0 | 0 | 0 | 0 | 0 | 0 |
| 94A | 0 | 0 | 0 | 0 | 0 | 0 | 0 | 0 | 0 | 0 | 0 | 0 |
| 95A | 0 | 0 | 0 | 0 | 0 | 0 | 0 | 0 | 0 | 0 | 0 | 0 |
| 96A | 0 | 0 | 0 | 0 | 0 | 0 | 0 | 0 | 0 | 0 | 0 | 0 |
| 97A | 0 | 0 | 0 | 0 | 0 | 0 | 0 | 0 | 0 | 0 | 0 | 0 |
| 98A | 0 | 0 | 0 | 0 | 0 | 0 | 0 | 0 | 0 | 0 | 0 | 0 |
| 99A | 0 | 0 | 0 | 0 | 0 | 0 | 0 | 0 | 0 | 0 | 0 | 0 |
| 100A | 0 | 0 | 0 | 0 | 0 | 0 | 0 | 0 | 0 | 0 | 0 | 0 |
| 101A | 0 | 0 | 0 | 0 | 0 | 0 | 0 | 0 | 0 | 0 | 0 | 0 |
| 102A | 0 | 0 | 0 | 0 | 0 | 0 | 0 | 0 | 0 | 0 | 0 | 0 |
| 103A | 0 | 0 | 0 | 0 | 0 | 0 | 0 | 0 | 0 | 0 | 0 | 0 |
| 104A | 0 | 0 | 0 | 0 | 0 | 0 | 0 | 0 | 0 | 0 | 0 | 0 |
| 105A | 0 | 0 | 0 | 0 | 0 | 0 | 0 | 0 | 0 | 0 | 0 | 0 |
| 106A | 0 | 0 | 0 | 0 | 0 | 0 | 0 | 0 | 0 | 0 | 0 | 0 |
| 107A | 0 | 0 | 0 | 0 | 0 | 0 | 0 | 0 | 0 | ± | 0 | 0 |
| 108A | 0 | 0 | 0 | 0 | 0 | 0 | 0 | 0 | 0 | 0 | 0 | 0 |
| 109A | 0 | 0 | 0 | 0 | 0 | 0 | 0 | 0 | 0 | 0 | 0 | 0 |
| 110A | 0 | 0 | 0 | 0 | 0 | 0 | 0 | 0 | 0 | 0 | 0 | 0 |
| 111A | 0 | 0 | 0 | 0 | 0 | 0 | 0 | 0 | 0 | 0 | 0 | 0 |

TABLE 1-continued

Summary of Dermal Scores

| Subject Number | Induction Scores | | | | | | | | | Challenge Scores | | |
|---|---|---|---|---|---|---|---|---|---|---|---|---|
| | 1 | 2 | 3 | 4 | 5 | 6 | 7 | 8 | 9 | 24 Hour | 48 Hour | 72 Hour |
| 112A | 0 | | | | | | Discontinued | | | | | |
| 1B | 0 | 0 | 0 | 0 | 0 | 0 | 0 | 0 | 0 | 0 | 0 | 0 |
| 2B | 0 | 0 | 0 | 0 | 0 | 0 | 0 | 0 | 0 | 0 | 0 | 0 |
| 3B | 0 | 0 | 0 | 0 | 0 | 0 | 0 | 0 | ± | 0 | 0 | 0 |
| 4B | 0 | 0 | 0 | 0 | 0 | 0 | 0 | 0 | | Discontinued | | |
| 5B | 0 | 0 | 0 | 0 | 0 | 0 | 0 | ± | 1+ | ± | 0 | 0 |
| 6B | 0 | 0 | 0 | 0 | 0 | 0 | 0 | 0 | 0 | 0 | 0 | 0 |
| 7B | 0 | 0 | 0 | 0 | 0 | 0 | 0 | 0 | 0 | 0 | 0 | 0 |
| 8B | 0 | 0 | 0 | 0 | 0 | 0 | 0 | 0 | 0 | 0 | 0 | 0 |
| 9B | 0 | 0 | 0 | 0 | 0 | 0 | 0 | 0 | 0 | 0 | 0 | 0 |
| 10B | 0 | 0 | 0 | 0 | 0 | 0 | 0 | 0 | 0 | 0 | 0 | 0 |
| 11B | 0 | 0 | 0 | 0 | 0 | 0 | 0 | 0 | 0 | 0 | 0 | 0 |
| 12B | 0 | 0 | 0 | 0 | 0 | 0 | 0 | 0 | 0 | 0 | 0 | 0 |
| 13B | 0 | 0 | 0 | 0 | 0 | 0 | 0 | 0 | 0 | 0 | 0 | 0 |
| 14B | 0 | 0 | 0 | 0 | 0 | 0 | 0 | 0 | 0 | 0 | 0 | 0 |
| 15B | 0 | 0 | 0 | 0 | 0 | 0 | 0 | 0 | 0 | 0 | 0 | 0 |
| 16B | 0 | 0 | 0 | 0 | 0 | 0 | 0 | 0 | 0 | 0 | 0 | 0 |
| 17B | 0 | 0 | 0 | 0 | 0 | 0 | 0 | 0 | 0 | 0 | ± | 0 |
| 18B | 0 | 0 | 0 | 0 | 0 | 0 | 0 | 0 | 0 | 0 | 0 | 0 |
| 19B | 0 | 0 | 0 | 0 | 0 | 0 | 0 | 0 | 0 | 0 | 0 | 0 |
| 20B | 0 | 0 | 0 | 0 | 0 | 0 | 0 | 0 | 0 | 0 | 0 | 0 |
| 21B | 0 | 0 | 0 | 0 | 0 | 0 | 0 | 0 | 0 | 0 | 0 | 0 |
| 22B | 0 | 0 | 0 | 0 | 0 | | | Discontinued | | | | |
| 23B | 0 | 0 | 0 | 0 | 0 | 0 | 0 | 0 | 0 | 0 | 0 | 0 |
| 24B | 0 | 0 | 0 | 0 | 0 | ± | ± | ± | 0 | 0 | 0 | 0 |
| 25B | 0 | 0 | 0 | 0 | 0 | 0 | 0 | 0 | 0 | 0 | 0 | 0 |
| 26B | 0 | 0 | 0 | 0 | 0 | 0 | 0 | 0 | 0 | 0 | 0 | 0 |
| 27B | 0 | 0 | 0 | 0 | 0 | 0 | 0 | 0 | 0 | 0 | 0 | 0 |
| 28B | 0 | 0 | 0 | 0 | 0 | 0 | 0 | 0 | 0 | 0 | 0 | 0 |
| 29B | 0 | 0 | 0 | 0 | 0 | 0 | 0 | 0 | 0 | 0 | 0 | 0 |
| 30B | 0 | 0 | 0 | 0 | 0 | 0 | 0 | 0 | 0 | 0 | 0 | 0 |
| 31B | 0 | 0 | 0 | 0 | 0 | 0 | 0 | 0 | 0 | 0 | 0 | 0 |
| 32B | 0 | 0 | 0 | 0 | 0 | 0 | 0 | 0 | 0 | 0 | 0 | 0 |
| 33B | 0 | 0 | 0 | 0 | 0 | 0 | 0 | 0 | 0 | 0 | 0 | 0 |
| 34B | 0 | 0 | 0 | 0 | 0 | 0 | | Discontinued | | | | |
| 35B | 0 | 0 | 0 | 0 | 0 | 0 | | Discontinued | | | | |
| 36B | 0 | 0 | 0 | 0 | | | Discontinued | | | | | |
| 37B | 0 | 0 | 0 | 0 | 0 | 0 | 0 | 0 | 0 | 0 | 0 | 0 |
| 38B | 0 | 0 | 0 | 0 | 0 | 0 | 0 | 0 | 0 | 0 | 0 | 0 |
| 39B | 0 | 0 | 0 | 0 | 0 | 0 | 0 | 0 | 0 | 0 | 0 | 0 |
| 40B | 0 | 0 | 0 | 0 | 0 | 0 | 0 | 0 | 0 | 0 | 0 | 0 |
| 41B | 0 | 0 | 0 | 0 | 0 | 0 | 0 | 0 | 0 | 0 | 0 | 0 |
| 42B | 0 | 0 | 0 | 0 | 0 | 0 | 0 | 0 | 0 | 0 | 0 | 0 |
| 43B | 0 | 0 | 0 | 0 | 0 | 0 | 0 | 0 | 0 | 0 | 0 | 0 |
| 44B | 0 | 0 | 0 | 0 | 0 | 0 | 0 | 0 | 0 | 0 | 0 | 0 |
| 45B | 0 | 0 | 0 | 0 | 0 | 0 | 0 | 0 | 0 | 0 | 0 | 0 |
| 46B | 0 | 0 | 0 | 0 | 0 | 0 | 0 | 0 | 0 | 0 | 1 + e | 1 + e* |
| 47B | 0 | 0 | 0 | 0 | 0 | 0 | 0 | 0 | 0 | 0 | 0 | 0 |
| 48B | 0 | 0 | 0 | 0 | 0 | 0 | 0 | 0 | 0 | 0 | 0 | 0 |
| 49B | 0 | 0 | 0 | 0 | 0 | 0 | 0 | 0 | 0 | 0 | 0 | 0 |
| 50B | 0 | 0 | 0 | 0 | 0 | 0 | 0 | 0 | 0 | 0 | 0 | 0 |
| 51B | 0 | 0 | 0 | 0 | 0 | 0 | 0 | 0 | 0 | 0 | 0 | 0 |
| 52B | 0 | 0 | 0 | 0 | 0 | 0 | 0 | 0 | 0 | 0 | 0 | 0 |
| 53B | 0 | 0 | 0 | 0 | 0 | 0 | 0 | 0 | 0 | 0 | 0 | 0 |
| 54B | 0 | 0 | 0 | 0 | 0 | 0 | 0 | 0 | 0 | 0 | 0 | 0 |
| 55B | 0 | 0 | 0 | 0 | 0 | 0 | 0 | 0 | 0 | 0 | 0 | 0 |
| 56B | 0 | 0 | 0 | 0 | 0 | 0 | 0 | 0 | 0 | 0 | 0 | 0 |
| 57B | 0 | 0 | 0 | 0 | 0 | 0 | 0 | 0 | 0 | 0 | 0 | 0 |
| 58B | 0 | 0 | 0 | 0 | 0 | 0 | 0 | 0 | 0 | 0 | 0 | 0 |
| 59B | 0 | 0 | 0 | 0 | 0 | 0 | 0 | 0 | 0 | 0 | 0 | 0 |
| 60B | 0 | 0 | 0 | 0 | 0 | 0 | 0 | 0 | 0 | 0 | 0 | 0 |
| 61B | 0 | 0 | 0 | 0 | 0 | 0 | 0 | 0 | 0 | 0 | 0 | 0 |
| 62B | 0 | 0 | 0 | 0 | 0 | 0 | 0 | 0 | 0 | 0 | 0 | 0 |
| 63B | 0 | 0 | 0 | 0 | 1+ | ± | 1+ | 1+ | ± | 0 | 0 | 0 |
| 64B | 0 | 0 | 0 | 0 | 0 | 0 | 0 | 0 | 0 | 0 | 0 | 0 |
| 65B | 0 | 0 | 0 | 0 | 0 | 0 | 0 | 0 | 0 | 0 | 0 | 0 |
| 66B | 0 | 0 | 0 | 0 | 0 | 0 | 0 | 0 | 0 | 0 | 0 | 0 |
| 67B | 0 | 0 | 0 | 0 | 0 | 0 | 0 | 0 | 0 | 0 | 0 | 0 |
| 68B | 0 | 0 | 0 | 0 | 0 | 0 | 0 | 0 | 0 | 0 | 0 | 0 |
| 69B | 0 | 0 | 0 | 0 | 0 | 0 | 0 | 0 | 0 | 0 | 0 | 0 |
| 70B | 0 | 0 | 0 | 0 | 0 | 0 | 0 | 0 | 0 | 0 | 0 | 0 |

TABLE 1-continued

Summary of Dermal Scores

| Subject Number | Induction Scores | | | | | | | | | Challenge Scores | | |
|---|---|---|---|---|---|---|---|---|---|---|---|---|
| | 1 | 2 | 3 | 4 | 5 | 6 | 7 | 8 | 9 | 24 Hour | 48 Hour | 72 Hour |
| 71B | | | | | | Discontinued | | | | | | |
| 72B | 0 | 0 | 0 | 0 | 0 | 0 | 0 | 0 | 0 | 0 | 0 | 0 |
| 73B | 0 | 0 | 0 | 0 | 0 | 0 | 0 | 0 | 0 | 0 | 0 | 0 |
| 74B | 0 | 0 | 0 | | | | Discontinued | | | | | |
| 75B | 0 | 0 | 0 | 0 | 0 | 0 | 0 | 0 | 0 | 0 | 0 | 0 |
| 76B | 0 | 0 | 0 | 0 | 0 | 0 | 0 | 0 | 0 | 0 | 0 | 0 |
| 77B | 0 | 0 | 0 | 0 | 0 | 0 | 0 | 0 | 0 | 0 | 0 | 0 |
| 78B | 0 | 0 | 0 | 0 | 0 | 0 | 0 | 0 | 0 | 0 | 0 | 0 |
| 79B | 0 | 0 | 0 | 0 | 0 | 0 | 0 | 0 | 0 | 0 | 0 | 0 |
| 80B | | | | | | Discontinued | | | | | | |
| 81B | 0 | 0 | 0 | 0 | 0 | 0 | 0 | 0 | 0 | 0 | 0 | 0 |
| 82B | 0 | 0 | 0 | 0 | 0 | 0 | 0 | 0 | 0 | 0 | 0 | 0 |
| 83B | 0 | 0 | 0 | 0 | 0 | 0 | 0 | 0 | 0 | 0 | 0 | 0 |
| 84B | 0 | 0 | 0 | 0 | 0 | 0 | 0 | ± | 0 | 0 | 0 | 0 |
| 85B | 0 | 0 | 0 | 0 | 0 | 0 | 0 | 0 | 0 | 0 | 0 | 0 |
| 86B | 0 | 0 | 0 | 0 | 0 | 0 | 0 | 0 | 0 | 0 | 0 | 0 |
| 87B | 0 | 0 | 0 | 0 | 0 | 0 | 0 | 0 | 0 | 0 | 0 | 0 |
| 88B | 0 | 0 | 0 | 0 | 0 | 0 | 0 | 0 | 0 | 0 | 0 | 0 |
| 89B | 0 | 0 | 0 | 0 | 0 | 0 | 0 | 0 | 0 | 0 | 0 | 0 |
| 90B | | | | | | Discontinued | | | | | | |
| 91B | | | | | | Pre-sensitized | | | | | | |
| 92B | 0 | 0 | 0 | 0 | 0 | 0 | 0 | 0 | 0 | 0 | 0 | 0 |
| 93B | 0 | 0 | 0 | 0 | 0 | 0 | 0 | 0 | 0 | 0 | 0 | 0 |
| 94B | 0 | 0 | 0 | 0 | 0 | 0 | 0 | 0 | 0 | 0 | 0 | 0 |
| 95B | 0 | 0 | 0 | 0 | 0 | 0 | 0 | 0 | 0 | 0 | 0 | 0 |
| 96B | ± | 0 | 0 | 0 | 0 | 0 | 0 | 0 | 0 | 0 | 0 | 0 |
| 97B | 0 | 0 | 0 | ± | ± | 1+ | 2 + c | 0 | 0 | 0 | 0 | 0 |
| 98B | 0 | 0 | 0 | 0 | 0 | 0 | 0 | 0 | 0 | 0 | 0 | 0 |
| 99B | 0 | 0 | 0 | 0 | 0 | 0 | 0 | 0 | 0 | 0 | 0 | 0 |
| 100B | 0 | 0 | 0 | 0 | 0 | 0 | 0 | 0 | 0 | 0 | 0 | 0 |
| 101B | 0 | 0 | 0 | 0 | 0 | 0 | 0 | 0 | 0 | 0 | 0 | 0 |
| 102B | 0 | 0 | 0 | 0 | 0 | 0 | 0 | 0 | 0 | 0 | 0 | 0 |
| 103B | 0 | 0 | 0 | 0 | 0 | 0 | 0 | 0 | 0 | 0 | 0 | 0 |
| 104B | 0 | 0 | 0 | 0 | 0 | 0 | 0 | 0 | 0 | 0 | 0 | 0 |
| 105B | 0 | 0 | 0 | 0 | 0 | 0 | 0 | 0 | 0 | 0 | 0 | 0 |
| 106B | 0 | 0 | 0 | 0 | 0 | 0 | 0 | 0 | 0 | 0 | 0 | 0 |
| 107B | 0 | 0 | 0 | 0 | 0 | 0 | 0 | 0 | 0 | 0 | 0 | 0 |
| 108B | 0 | 0 | 0 | 0 | 0 | 0 | 0 | 0 | 0 | 0 | 0 | 0 |
| 109B | 0 | 0 | 0 | 0 | 0 | 0 | 0 | 0 | 0 | 0 | 0 | 0 |
| 110B | 0 | 0 | 0 | 0 | 0 | 0 | 0 | 0 | 0 | 0 | 0 | 0 |
| 111B | 0 | 0 | 0 | 0 | 0 | 0 | 0 | 0 | 0 | 0 | 0 | 0 |
| 112B | 0 | 0 | 0 | 0 | 0 | 0 | 0 | 0 | 0 | 0 | 0 | 0 | e = Edema
*A 1+ level reaction was observed at the 96 hour reading
c = Changed Site The test results show almost zero irritation caused by the minoxidil formula (Vitadil/Nutrisol Formulation) of the invention. This is in marked contrast to commercial preparations of minoxidil that are well-established as causing itching, drying and scaling of the skin for almost all of the users to some extent.

Example 2

Evaporative Loss of Minoxidil Solution

In this test, a petri dish containing 1 mL of the minoxidil formulation was introduced into a heated chamber maintained at 37° C. to monitor evaporative loss over time. Comparative testing was conducted for a minoxidil formulation (the above-described Vitadil/Nutrisol Formulation) in accordance with the present invention (Sample A), and a commercially available minoxidil Rogaine® formulation (Sample B).

The dish containing the minoxidil formulation was introduced into a heated chamber maintained at body temperature (37° C.±0.5° C.), with the petri dish positioned on an electronic scale with a digital readout.

The total weight of the petri dish and minoxidil formulation was recorded at the start of the test, and at intervals of 30 seconds, 1 minute, 2 minutes, 5 minutes, 10 minutes and 15 minutes. The tare weight of the petri dish was subtracted from the total weight values to obtain the weight of the minoxidil formulation in the petri dish at the time of measurement.

The test was repeated three times (Sample A: first run, S1-1; second run, S1-2; third run, S1-3; and Sample B: first run, U1-1; second run, U1-2; third run, U1-3).

The results are shown in Table 2 (Sample A, formulation of the present invention) and Table 3 (Sample B, Rogaine® formulation) below, and a graph of the comparative results is contained in FIG. 1, wherein curve A is the curve for the (Sample A) formulation of the present invention, and curve B is the curve for the prior art Rogaine® formulation.

TABLE 2

Formulation of the Present Invention (Sample A)

| time | S1-1 | S1-2 | S1-3 | remark |
|---|---|---|---|---|
| 0 | 10.6013 | 10.0633 | 10.6443 | initial weight |
| 30 sec | 10.5741 | 9.9945 | 10.5987 | initial weight |
| 1 min | 10.5523 | 9.9585 | 10.5523 | initial weight |
| 2 min | 10.5310 | 9.9182 | 10.5214 | initial weight |
| 5 min | 10.3982 | 9.8862 | 10.4530 | initial weight |
| 10 min | 10.3320 | 9.8025 | 10.3891 | initial weight |
| 15 min | 10.3145 | 9.7857 | 10.3657 | initial weight | evaporation loss

| time | S1-1 | S1-2 | S1-3 | average |
|---|---|---|---|---|
| 0 | 0.0000 | 0.0000 | 0.0000 | 0.0000 |
| 30 sec | 0.0272 | 0.0688 | 0.0456 | 0.0472 |
| 1 min | 0.0490 | 0.1048 | 0.0920 | 0.0819 |
| 2 min | 0.0703 | 0.1451 | 0.1229 | 0.1128 |
| 5 min | 0.2031 | 0.1771 | 0.1913 | 0.1905 |
| 10 min | 0.2693 | 0.2608 | 0.2552 | 0.2618 |
| 15 min | 0.2868 | 0.2776 | 0.2786 | 0.2810 |
| loss (%) | 28.68 | 27.76 | 27.86 | 28.10 |

TABLE 3

5% minoxidil Rogaine ® formulation (Sample B)

| time | U1-1 | U1-2 | U1-3 | remark |
|---|---|---|---|---|
| 0 | 9.9520 | 9.4343 | 10.0182 | initial weight |
| 30 sec | 9.9027 | 9.3763 | 9.9475 | initial weight |
| 1 min | 9.8638 | 9.3024 | 9.9057 | initial weight |
| 2 min | 9.7681 | 9.2777 | 9.8350 | initial weight |
| 5 min | 9.6421 | 9.1767 | 9.7991 | initial weight |
| 10 min | 9.5859 | 9.0982 | 9.7199 | initial weight |
| 15 min | 9.5639 | 9.0740 | 9.6899 | initial weight | evaporation loss

| time | U1-1 | U1-2 | U1-3 | average |
|---|---|---|---|---|
| 0 | 0.0000 | 0.0000 | 0.0000 | 0.0000 |
| 30 sec | 0.0493 | 0.0580 | 0.0707 | 0.0593 |
| 1 min | 0.0882 | 0.1319 | 0.1125 | 0.1109 |
| 2 min | 0.1839 | 0.1566 | 0.1832 | 0.1746 |
| 5 min | 0.3099 | 0.2576 | 0.2191 | 0.2622 |
| 10 min | 0.3661 | 0.3361 | 0.2983 | 0.3335 |
| 15 min | 0.3881 | 0.3603 | 0.3283 | 0.3589 |
| loss (%) | 38.81 | 36.03 | 32.83 | 35.89 |

The results show that the formulation of the present invention exhibited substantially reduced evaporative loss in relation to the commercial Rogaine formula.

Example 3

Blood Concentration Levels of Minoxidil Subsequent to Administration of Minoxidil Formulation of the Invention, and Prior Art Minoxidil Formulation Three healthy male subjects were involved in this experiment. The subjects had used the formulation of the invention (the above-described Vitadil/Nutrisol Formulation) daily for at least eight months.

All subjects administered the formulation by topical application to the scalp daily, in an amount of 30 mg per day of the active minoxidil ingredient, with brief massaging of the topical formulation into the scalp.

To determine systemic penetration, blood samples were drawn from each subject, and the blood was analyzed by a commercial analysis laboratory (NMS Labs, Willow Grove, Pa.) by high-performance liquid chromatography (HPLC), to determine blood level of minoxidil.

In the use of commercially available prior art minoxidil formulations, the following is a reported and generally recognized antihypertensive profile:

---

Minoxidil

---

Synonym(s): Loniten ®, Minodyl ® and Rogaine ®
Antihypertensive: 1 hour peak after 5 mg starting dose: 60 ng/mL plasma; steady-state during chronic 30 mg/day: 250 ng/ML peak, 40 ng/mL trough.
Antihypertensive effects decline by 30% per day after last dose.
Topical hair growth stimulant: 1 mL 2% b.i.d. dose:
Less than 2-30 ng/ML plasma.

---

The blood samples of the test subjects using the formulation of the present invention, taken one hour after administration of the most recent dose of the formulation in order to yield peak values, were subjected to HPLC analysis with a chromatographic instrument having a 8.0 nanograms/milliliter detection limit.

As compared to the 250 ng/mL peak level of daily users of prior art commercial minoxidil formulations, the blood samples of the three test subjects taken one hour after administration of the most recent dose of the formulation of the invention detected no presence of minoxidil.

Accordingly, the minoxidil formulations of the present invention exhibit an unexpected and striking reduction of systemic penetration, as evidenced by blood level concentrations below the 8.0 ng/ML detection limit of the HPLC instrument, contrasted with the 250 ng/ML level concentration characteristic of users of prior art commercial minoxidil formulations.

Example 4

Heart Palpitation and Scalp Irritation Study

In this study, a commercially available topical minoxidil formulation (Rogaine®) and a topical minoxidil formulation of the present invention (the above-described Vitadil/Nutrisol Formulation) were comparatively tested to determine incidence of heart palpitation in subjects 10-30 minutes after use, and incidence of scalp irritation 1-2 hours after use.

This study was undertaken in view of the well-documented side effects of commercially available minoxidil formulations, involving occurrence of heart palpitations in a substantial number of users within 30 minutes of administration of the formulation to the scalp, and occurrence of significant scalp irritation within 1-2 hours after administration of the formulation to the scalp.

In each instance, the test subject administered 1 cc of the formulation to the scalp in a usual manner involving massaging of the formulation onto the scalp.

The results are set out below in Table 4 for the Rogaine® minoxidil formulation, and in Table 5 for the Vitadil/Nutrisol Formulation of the present invention.

TABLE 4

Heart Palpitation/Scalp Irritation After Administration of 1 cc of Topical Minoxidil Rogaine ® Formulation

| Subject Number | Age/Gender | Heart palpitation 10-30 minutes after use | Scalp irritation 1-2 hours after use |
|---|---|---|---|
| 1 | 34/male | Slight heart palpitation | Slight scalp irritation |
| 2 | 28/male | No palpitation experienced | Slight scalp irritation |
| 3 | 34/male | No palpitation experienced | Scalp irritation |
| 4 | 29/male | Slight part palpitation/swollen hands | Slight scalp irritation |
| 5 | 52/male | Heart palpitation/swollen hands | Moderate scalp irritation |
| 6 | 28/female | Moderate heart palpitation | No irritation experienced |
| 7 | 68/female | Heart palpitation/swollen hands | No irritation experienced |
| 8 | 52/female | No palpitation experienced | Slight scalp irritation |
| 9 | 42/female | Slight heart palpitation | No irritation experienced |

TABLE 5

Heart Palpitation/Scalp Irritation After Administration of 1 cc of Topical Vitadil/Nutrisol Formulation

| Subject Number | Age/Gender | Heart palpitation 10-30 minutes after use | Scalp irritation 1-2 hours after use |
|---|---|---|---|
| 1 | 42/male | none | none |
| 2 | 40/male | none | none |
| 3 | 29/male | none | none |
| 4 | 34/male | none | none |
| 5 | 46/male | none | none |
| 6 | 30/female | none | none |
| 7 | 60/female | none | none |
| 8 | 22/female | none | none |

The results showed that the minoxidil formulation of the present invention (Vitadil/Nutrisol Formulation) achieved a substantial improvement over the Rogaine® formulation in the test population. A substantial portion of the test subjects who administered the Rogaine® formulation to their scalps experienced heart palpitations and/or scalp irritation, while the test subjects who administered the formulation of the present invention experienced no incidences of heart palpitation or scalp irritation.

Example 5

Administered Formulation Scalp Retention Study

In this study, a commercially available topical minoxidil formulation (Rogaine®) and a topical minoxidil formulation of the present invention (Vitadil/Nutrisol Formulation) were comparatively tested to determine retention of the formulation on the scalp, as determined by videotaping of scalp areas to which the formulations had been applied by the respective test subjects.

One cc of the commercially available topical minoxidil formulation (Rogaine®) was administered to the scalp of the test subject, and the scalp was videotaped, over a period of nine seconds, to determine whether the formulation remained in a liquid state or not, in consequence of solvent evaporation from the applied formulation.

The same test was conducted with administration of 1 cc of a topical minoxidil formulation of the present invention (Vitadil/Nutrisol Formulation) to the scalp of the test subject, and scalp was videotaped over a period of nine seconds, to correspondingly determine whether the formulation remained in a liquid state, in consequence of solvent evaporation from the applied formulation.

Seven persons were used as test subjects for the commercially available topical minoxidil formulation (Rogaine®), and 10 persons were used as the test subjects for the topical minoxidil formulation of the present invention (Vitadil/Nutrisol Formulation).

As soon as the formulation was applied to the scalp of the specific user, close-up videotaping of the scalp region was initiated, and continued for nine seconds.

Viewing of the videotapes of the administered commercial minoxidil formulation (Rogaine®) showed that the applied formulation was initially liquid, but by the end of the 9-second videotape, the formulation had assumed a dry, powdered appearance.

Viewing of the videotapes of the administered minoxidil formulation of the present invention (Vitadil/Nutrisol Formulation) showed that the applied formulation remained wet in character throughout the 9-second videotape.

Thus, the formulation including the carrier composition of the invention of the invention exhibited a liquid appearance throughout the duration of the videotaped segment, whereas the prior art minoxidil formulation exhibited a rapid progression to dryness during the same period of observation.

These results show that the evaporative loss was substantially reduced in the formulation of the invention, relative to the prior art formulation. This is significant, since when a minoxidil formulation reaches a state of dryness there is little or no ability of the active minoxidil ingredient to penetrate into the hair follicle. Accordingly, by maintaining a liquid state of the minoxidil-containing formulation on the scalp of the user, the minoxidil formulation containing the carrier composition of the present invention achieves an enhanced efficacy of the minoxidil.

Example 6

Anagen Hair Test

In this test, TrichoScan analysis of anagen phase hair growth (the anagen phase being the active growth phase of hair follicles, when cells in the root of the hair are dividing rapidly, adding to the hair shaft) was carried out, to determine the efficacy of a hair growth formulation of the present invention in stimulating the growth of anagen phase hair.

The TrichoScan procedure was carried out in a manner as described in Hoffman, R., "TrichoScan: a novel tool for the analysis of hair growth in vivo," J. Investig. Dermatol. Symp. Proc., 2003 June, 8(1): 109-15.

Subjects in the test study used a minoxidil formulation of the present invention (Vitadil/Nutrisol Formulation), which was applied in an amount of 1 cc, twice daily. In the following tables, the baseline interval represented the beginning of the test, with the 48 hour reading at such point being prior to any administration of the minoxidil formulation.

Table 8 shows the number of anagen hairs in the test area at such point, as well as the number of anagen hairs as measured at 48 hours after the two-month interval (two months after inception of daily use of the minoxidil formulation), the number of anagen hairs as measured at 48 hours after the four-month interval (four months after inception of daily use of the minoxidil formulation), and the number of anagen hairs as measured at 48 hours after the six month interval (six months after inception of daily use of the minoxidil formulation).

TABLE 8

TrichoScan Analysis of Anagen Hairs

| Subject Number | Number of Anagen Hairs At 48 Hours Following the 2 Month Interval | | % Change from 48 Hours Following the |
|---|---|---|---|
| | 48 Hours following the Baseline Interval | 48 Hours following the 2 Month Interval | Baseline Interval 48 Hours following the 2 Month Interval |
| 5 | 31 | 34 | 10% |
| 8 | 28 | 38 | 36% |
| 12 | 37 | 43 | 16% |
| 13 | 34 | 39 | 15% |
| 14 | 33 | 46 | 39% |
| 16 | 28 | 34 | 21% |
| 20 | 18 | 26 | 44% |
| 21 | 28 | 45 | 61% |
| 27 | 25 | 30 | 20% |
| 29 | 23 | 39 | 70% |
| 30 | 22 | 30 | 36% |
| 31 | 36 | 37 | 3% |
| 35 | 24 | 30 | 25% |
| Mean | 28 | 36 | 30% |
| Std. Dev. | 6 | 6 | 20% |

| Subject Number | Number of Anagen Hairs At 48 Hours Following the 4 Month Interval | | % Change from 48 Hours Following the |
|---|---|---|---|
| | 48 Hours following the Baseline Interval | 48 Hours following the 4 Month Interval | Baseline Interval 48 Hours following the 4 Month Interval |
| 1 | 37 | 39 | 5% |
| 4 | 32 | 34 | 6% |
| 5 | 31 | 31 | 0% |
| 7 | 38 | 40 | 5% |
| 8 | 28 | 34 | 21% |
| 10 | 28 | 50 | 79% |
| 11 | 44 | 58 | 32% |
| 13 | 34 | 48 | 41% |
| 14 | 33 | 50 | 52% |
| 16 | 28 | 35 | 25% |
| 18 | 29 | 52 | 79% |
| 20 | 18 | 21 | 17% |
| 21 | 28 | 42 | 50% |
| 26 | 28 | 33 | 18% |
| 27 | 25 | 31 | 24% |
| 29 | 23 | 32 | 39% |
| 31 | 36 | 45 | 25% |
| 35 | 24 | 31 | 29% |
| 36 | 19 | 22 | 16% |
| 37 | 21 | 22 | 5% |
| Mean | 29 | 38 | 28% |
| Std. Dev. | 7 | 11 | 23% |

| Subject Number | Number of Anagen Hairs At 48 Hours Following the 6 Month Interval | | % Change from 48 Hours Following the |
|---|---|---|---|
| | 48 Hours following the Baseline Interval | 48 Hours following the 6 Month Interval | Baseline Interval 48 Hours following the 6 Month Interval |
| 1 | 37 | 51 | 38% |
| 4 | 32 | 40 | 25% |
| 5 | 31 | 50 | 61% |
| 6 | 37 | 45 | 22% |
| 7 | 38 | 41 | 8% |
| 8 | 28 | 32 | 14% |
| 10 | 28 | 41 | 46% |
| 11 | 44 | 53 | 20% |
| 12 | 37 | 43 | 16% |
| 13 | 34 | 41 | 21% |
| 14 | 33 | 42 | 27% |
| 17 | 46 | 53 | 15% |
| 18 | 29 | 34 | 17% |
| 20 | 18 | 23 | 28% |
| 21 | 28 | 37 | 32% |
| 25 | 37 | 45 | 22% |
| 29 | 23 | 26 | 13% |
| 35 | 24 | 35 | 46% |
| Mean | 32 | 41 | 26% |
| Std. Dev. | 7 | 9 | 14% |

Table 9 is a composite tabulation of the data from Table 8, identifying the number and percentage of subjects that improved in anagen hair count, the percent change at two months, four months and six months, and the P-values for these determinations, showing the statistically significant improvement achieved by the minoxidil formulation of the present invention.

TABLE 9

Statistical Analysis of TrichoScan - Anagen Hairs

| Parameter | Time Interval | Number of Subjects that Improved | Mean of % Change from 48 Hours Following the Baseline Interval | P-Value |
|---|---|---|---|---|
| Number of Anagen Hairs | 48 Hours following the Month 2 Study Visit | 13 of 32 (41%) | 30% | 0.0001* |
| | 48 Hours following the Month 4 Study Visit | 20 of 32 (63%) | 28% | <0.0001* |
| | 48 Hours following the Month 6 Study Visit | 18 of 32 (56%) | 26% | <0.0001* |

*Statistically Significant Improvement

While the invention has been described herein with respect to particular aspects, features and embodiments, it will be recognized that the invention is not thus limited, and contemplates additional compositions, formulations, and methods of formulation and use, beyond the specific description herein. Accordingly, the invention is intended to be broadly construed, as including such variations, modifications and alternative embodiments as may readily suggest themselves to those of ordinary skill in the art, based on the disclosure herein.

What is claimed is:

1. A method of promoting hair growth on a scalp region of a subject, said method comprising topically administering to the scalp region a minoxidil formulation, containing:
   (a) 1-10 wt. % minoxidil, based on total weight of the formulation;
   (b) 10-50 wt. % ethanol, based on total weight of the formulation;
   (c) 26-40 wt. % propylene glycol, based on total weight of the formulation;
   (d) from 0 to 3 wt. %, based on total weight of the formulation, of one or more of optional ingredients selected from the group consisting of retinol, retinoid compounds, betasitosterol, panthenol, 1,3-Dimethylol-5,5-dimethylhydantoin (DMDM hydantoin), biotin, cystine, sabal seralata fruit extract, and methyl paraben; and
   (e) a carrier composition, containing 40-70 wt. % water, 20-40 wt. % glycerin, and 5-15 wt. % polysorbate-80, based on total weight of the carrier composition,
   wherein amounts of minoxidil, ethanol, propylene glycol, optional ingredients, and carrier composition total to 100 wt. % of the formulation; and wherein the carrier is present in said formulation in an amount of 22-90% by weight, based on total weight of the formulation.

2. The method of claim 1, wherein the minoxidil formulation further comprises retinol.

3. The method of claim 1, wherein the minoxidil formulation further comprises retinoid compounds.

4. The method of claim 1, wherein the minoxidil formulation further comprises betasitosterol.

5. The method of claim 1, wherein the minoxidil formulation further comprises panthenol.

6. The method of claim 1, wherein the minoxidil formulation further comprises 1,3-Dimethylol-5,5-dimethylhydantoin (DMDM hydantoin).

7. The method of claim 1, wherein the minoxidil formulation further comprises biotin.

8. The method of claim 1, wherein the minoxidil formulation further comprises cystine.

9. The method of claim 1, wherein the minoxidil formulation further comprises sabal seralata fruit extract.

10. The method of claim 1, wherein the minoxidil formulation further comprises methyl paraben.

* * * * *

UNITED STATES PATENT AND TRADEMARK OFFICE
CERTIFICATE OF CORRECTION

| | |
|---|---|
| PATENT NO. | : 8,119,111 B2 |
| APPLICATION NO. | : 12/831241 |
| DATED | : February 21, 2012 |
| INVENTOR(S) | : Shane Malek |

It is certified that error appears in the above-identified patent and that said Letters Patent is hereby corrected as shown below:

Column 1, lines 5-6: "CROSS REFERENCE TO RELATED APPLICATION" should be -- CROSS REFERENCE TO RELATED APPLICATIONS --.

Column 1, lines 17-19: "Priority of U.S. patent application Ser. No. 11/305,647 and U.S. patent application Ser. No. 11/305,647..." should be -- Priority of U.S. patent application Ser. No. 11/610,322 and U.S. patent application Ser. No. 11/305,647... --.

Column 1, lines 20-22: "The disclosures of U.S. patent application Ser. No. 11/305,647 and U.S. patent application Ser. No. 11/305,647..." should be -- The disclosures of U.S. patent application Ser. No. 11/610,322 and U.S. patent application Ser. No. 11/305,647... --.

Signed and Sealed this
Tenth Day of July, 2012

David J. Kappos
*Director of the United States Patent and Trademark Office*

UNITED STATES PATENT AND TRADEMARK OFFICE
CERTIFICATE OF CORRECTION

Page 1 of 1

PATENT NO.         : 8,119,111 B2
APPLICATION NO.    : 12/831241
DATED              : February 21, 2012
INVENTOR(S)        : Shane Malek It is certified that error appears in the above-identified patent and that said Letters Patent is hereby corrected as shown below:

Column 1, lines 5-6: "CROSS REFERENCE TO RELATED APPLICATION" should be -- CROSS REFERENCE TO RELATED APPLICATIONS --.

Column 1, lines 10-12: "TOPICAL ADMINISTRATION CARRIER COMPOSITION AND THERAPEUTIC FORMULATIONS COMPRISING SAME" should be -- "TOPICAL ADMINISTRATION CARRIER COMPOSITION AND THERAPEUTIC FORMULATIONS COMPRISING SAME" --.

Column 1, lines 17-19: "Priority of U.S. patent application Ser. No. 11/305,647 and U.S. patent application Ser. No. 11/305,647..." should be -- Priority of U.S. patent application Ser. No. 11/610,322 and U.S. patent application Ser. No. 11/305,647... --.

Column 1, lines 20-22: "The disclosures of U.S. patent application Ser. No. 11/305,647 and U.S. patent application Ser. No. 11/305,647..." should be -- The disclosures of U.S. patent application Ser. No. 11/610,322 and U.S. patent application Ser. No. 11/305,647... --.

This certificate supersedes the Certificate of Correction issued July 10, 2012.

Signed and Sealed this
Fourteenth Day of August, 2012

David J. Kappos
*Director of the United States Patent and Trademark Office*